(12) United States Patent
Lia et al.

(10) Patent No.: US 6,746,406 B2
(45) Date of Patent: Jun. 8, 2004

(54) BLOOD PRESSURE MEASURING APPARATUS

(75) Inventors: Raymond A. Lia, Auburn, NY (US); Robert L. Vivenzio, Auburn, NY (US); Dominick Danna, Syracuse, NY (US); Raymond P. Dromms, Liverpool, NY (US); Scott S. Stearns, Marietta, NY (US); James M. Baxter, Jordan, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 51 days.

(21) Appl. No.: 10/025,159

(22) Filed: Dec. 19, 2001

(65) Prior Publication Data

US 2003/0114765 A1 Jun. 19, 2003

(51) Int. Cl.[7] .................................................. A61B 5/00
(52) U.S. Cl. ...................................................... 600/499
(58) Field of Search .............................. 600/499, 493.6, 600/490; 606/202

(56) References Cited

U.S. PATENT DOCUMENTS

| | | | | |
|---|---|---|---|---|
| 3,279,459 A | * | 10/1966 | Schenker | ..................... 600/499 |
| 3,633,567 A | | 1/1972 | Sarnoff | |
| 3,906,937 A | | 9/1975 | Aronson | |
| 4,549,550 A | * | 10/1985 | Kami | .......................... 600/499 |
| 4,920,971 A | * | 5/1990 | Blessinger | .................... 600/492 |
| 5,396,894 A | * | 3/1995 | Eide et al. | ..................... 600/499 |
| 5,413,582 A | * | 5/1995 | Eaton | .......................... 606/202 |
| 5,966,829 A | | 10/1999 | Lia et al. | |
| 6,036,718 A | | 3/2000 | Ledford et al. | |
| 6,120,458 A | | 9/2000 | Lia et al. | |
| 6,168,566 B1 | * | 1/2001 | Lia et al. | ..................... 600/488 |
| 6,245,024 B1 | | 6/2001 | Montagnino et al. | |
| 6,422,086 B1 | * | 7/2002 | Dromms et al. | ............ 713/715 |

FOREIGN PATENT DOCUMENTS

GB 740181 11/1955

OTHER PUBLICATIONS

Operating Instruction Manual, "Welch Allyn ® DuraShock ™ Integrated Aneroid Sphygmomanometer", pp. 1–7, © 2001.

* cited by examiner

*Primary Examiner*—Robert L. Nasser
(74) *Attorney, Agent, or Firm*—Wall Marjama & Bilinski LLP

(57) ABSTRACT

A blood pressure measuring apparatus includes an inflatable sleeve adapted to be wrapped about a limb of a patient. The sleeve includes an interior and at least one socket provided on an exterior surface of the sleeve, the socket being fluidly connected to the interior of the sleeve. A gage is directly attached to the sleeve socket through attachment of a mating engagement portion. A pneumatic bulb is also attached fluidly to the sleeve through a receiving port which is provided on at least one of the socket and the gage.

9 Claims, 5 Drawing Sheets

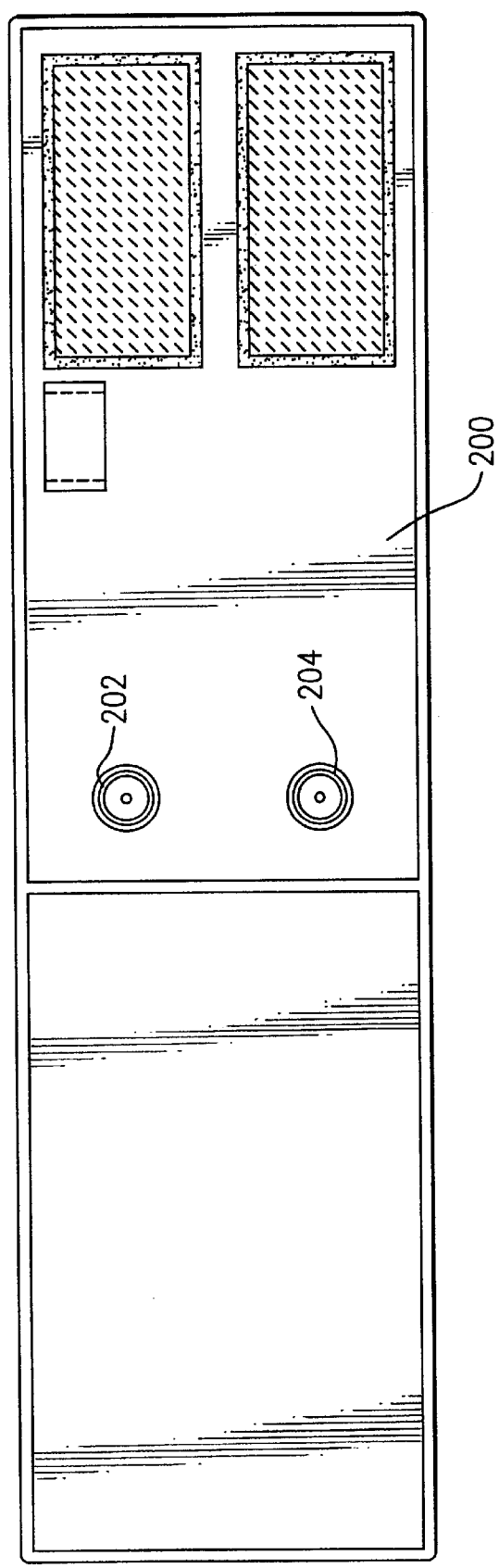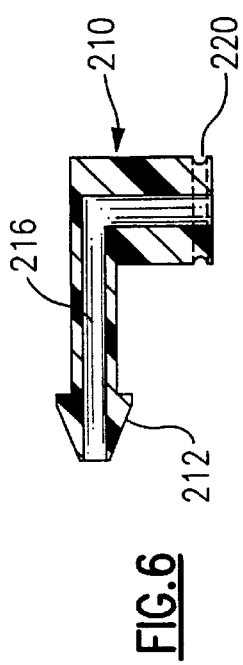
FIG.5
FIG.6

BLOOD PRESSURE MEASURING APPARATUS

FIELD OF THE INVENTION

This invention is directed to the field of medical diagnostic instruments, and in particular to a preferred interconnection between a gage housing and an inflatable sleeve of a blood pressure measuring apparatus.

BACKGROUND OF THE INVENTION

Typical blood pressure measuring instruments include an inflatable sleeve which is wrapped about the limb (i.e., arm or leg) of a patient. A pneumatic bulb is tethered by a hose and is fully interconnected to the sleeve interior. A gage which includes a dial face having a set of indicia is separately interconnected also by means of a hose to the sleeve interior. The gage includes an interior movement mechanism which is responsive to changes in pressure within the sleeve interior. The pressure changes produce circumferential movement of an indicating member attached to the movement mechanism relative to the set of indicia on the dial face of the gage.

Both the gage and the pneumatic bulb are tethered individually to the sleeve which includes corresponding barbs or receiving ports which permit fluid communication with the interior of the sleeve.

More recently, Applicants have devised a blood pressure measuring apparatus, such as described in copending U.S. Ser. No. 09/669,474, the entire contents of which are incorporated by reference in which the gage is directly attached to a port or socket which is integrally provided in the inflatable sleeve. This form of attachment is advantageous because the apparatus is far more compact than previously known devices of this type. Furthermore, the attachment eliminates any need for hoses between the gage and the inflatable sleeve. Moreover, the gage can be rotatably attached to the socket/sleeve permitting both left and right limb attachment and also allowing both a care giver and the patient to easily read the dial face of the gage and perform a blood pressure measurement.

There is still a general need in the field, however, to further simplify the manufacture and design of a blood pressure measuring apparatus.

SUMMARY OF THE INVENTION

According to an embodiment of the invention, there is described a blood pressure measuring apparatus comprising an inflatable sleeve having at least one port and a pneumatic bulb tethered to said sleeve through a hose, one end of said hose being attached to said pneumatic bulb and a remaining end of said hose being attached to a port on said sleeve. The measuring apparatus further includes a gage having a dial face with readable indicia and a movement mechanism which is responsive to fluid pressure changes in said sleeve, said gage being directly attached to said at least one socket of said inflatable sleeve, the socket permitting one end of the gage to be directly connected to the sleeve without the use of a hose.

A port is provided to receive the hose end extending from the pneumatic bulb wherein this receiving port can be provided on at least one of the sleeve socket and the gage.

In either instance, and by providing the receiving port on either the socket or the gage which directly mounts to the inflatable sleeve, the design and manufacturability of a blood pressure measuring apparatus is greatly simplified in comparison to previously known apparatus of this type.

According to another embodiment of the invention, there is described a blood pressure measuring apparatus including an inflatable sleeve having at least one port sized for directly receiving a gage wherein the gage includes an engagement portion which is sealingly fitted into said at least one port. The gage further includes a receiving port for receiving fluid input from a pneumatic means, such as a depressible bulb which is attached thereto.

According to yet another embodiment of the invention, there is disclosed a blood pressure measuring apparatus including an inflatable sleeve containing a pair or sockets each sized for receiving the mating end of a gage. A receiving port is provided on at least one of the sockets or the gage to permit attachment of a depressible bulb or other pneumatic means used to inflate the sleeve.

BRIEF DESCRIPTION OF THE DRAWINGS

For a further understanding of the invention, reference will be made to the following Detailed Description which is to be read in connection with the accompanying drawings, wherein:

FIG. 5 is a top elevational view of a sleeve of a blood pressure measuring apparatus made in accordance with a third embodiment of the invention, and FIG. 6 is a sectioned view of a port adapter which can be attached to the sleeve of FIG. 5.

DETAILED DESCRIPTION

Figure 1:
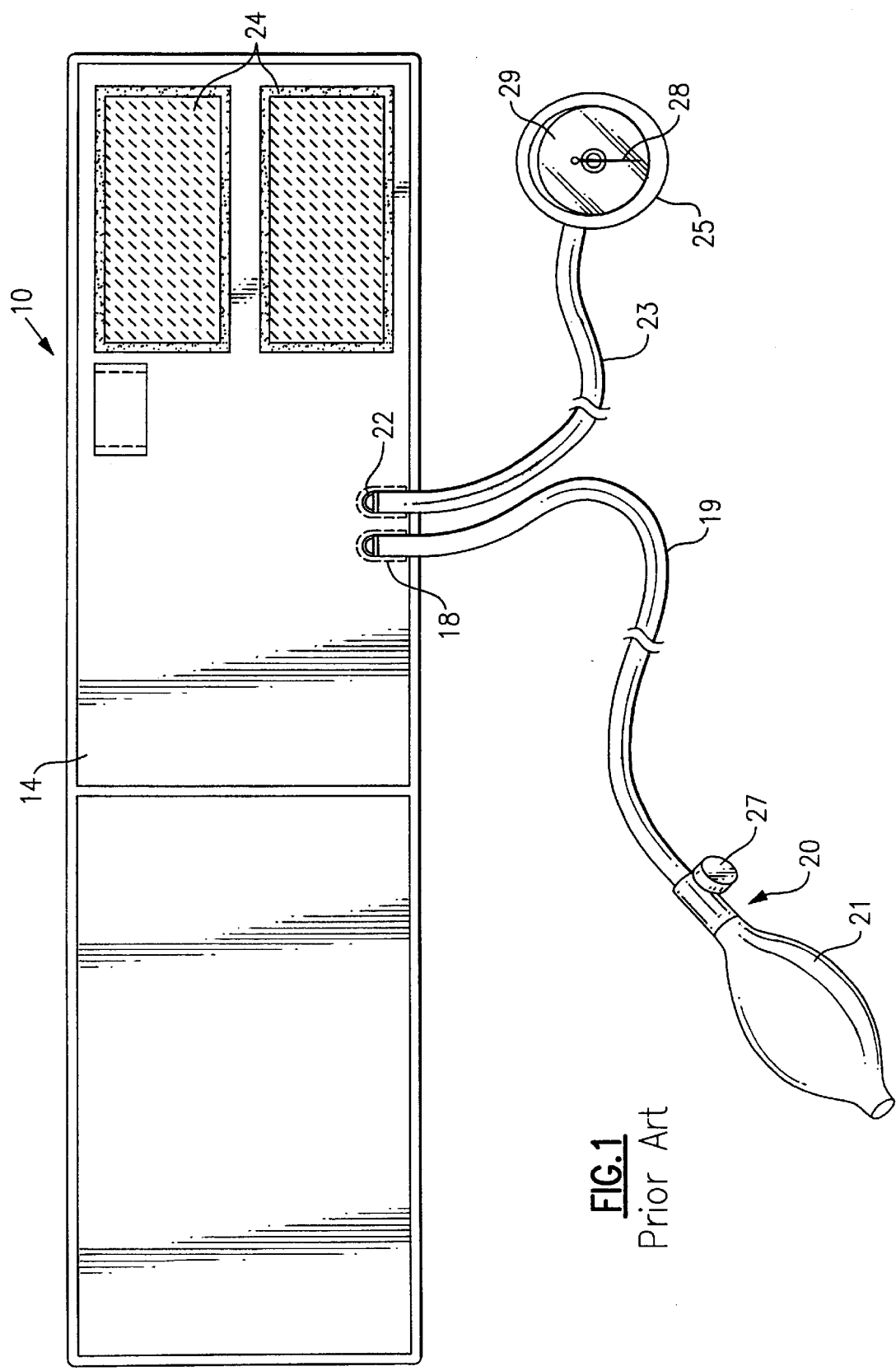
FIG. 1 is a top perspective view of a prior art blood pressure measuring apparatus.

Referring to FIG. 1, there is shown a prior art blood pressure measuring device or apparatus 10. An inflatable sleeve 14 made from a fluid impermeable material includes a pair of ports 18, 22 which engage hoses 19, 23 interconnecting the interior of the inflatable sleeve with a pneumatic assembly 20 and a gage 25, respectively. The sleeve 14 is wrapped around a limb of a patient using a set of hook and loop fasteners 24 and is subsequently inflated by squeezing a depressible bulb 21 which supplies air through the tethered hose 19 to the interior of the sleeve. As air enters the interior of the sleeve, a movement mechanism (not shown in this Fig.) provided within the interior of the gage 25 causes a corresponding circumferential movement of an indicating member 28 relative to indicia provided on a dial face 29. Following sufficient inflation of the wrapped sleeve 14, the sleeve 14 is deflated using a bleed valve 27 of the pneumatic assembly 20 and a blood pressure measurement is taken using a stethoscope (not shown) which is applied over the brachial artery of the patient in conjunction with the readings taken from the tethered gage 25 in a manner which is conventionally known.

Figure 2:
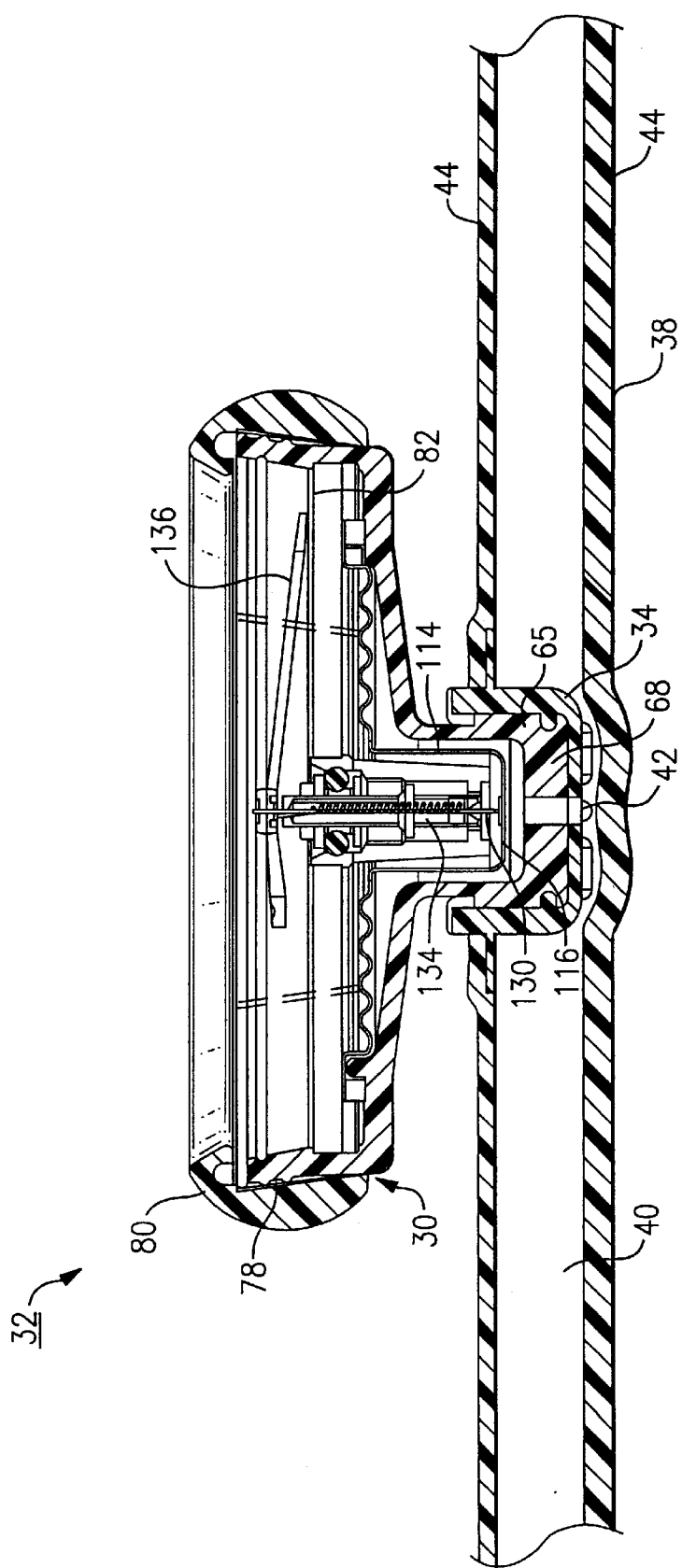
FIG. 2 is a side elevational view, in section of a prior art blood pressure measuring apparatus.

A second prior art blood pressure measuring device 32 is partially shown in FIG. 2. In this instance, and rather than employing a hose in connection therewith, a mating end of a gage 30 is directly and sealingly engaged within a socket 34 that is provided in an inflatable sleeve 38. In this embodiment, the inflatable sleeve 38 includes an interior 40, the sleeve being made from a pair of sleeve portions 44, which are RF welded or otherwise attached together. A specific type of sleeve which can be used for purposes of the present invention is described in U.S. Pat. No. 6,036,718, the entire contents of which are incorporated by reference, though it should be appreciated that other sleeve designs can be utilized. The socket 34 is defined through a slot provided in one of the sleeve portions 44 and includes a open-ended cylindrical cavity having a bottom opening 42 that fluidly interconnects the interior 40 of the sleeve 38 with the interior of an attached gage 30.

The gage 30 illustrated in FIG. 2 is herein described in greater detail, and includes an upper portion 78 which supports a dial face 82 having a set of measurement indicia (not shown) and a lower engagement portion 65 which is received directly by the socket 34. A peripheral bumper 80 is fitted about the upper portion 78 of the gage 30 to protect the contained movement mechanism from shock or impact loads. The gage 30 includes an interior sized for retaining the movement mechanism which includes a diaphragm 114 having a movable surface 116 that is responsive to pressure changes within the interior 40 of the sleeve 38. This movement mechanism is herein described in greater detail with regard to the operation of the herein described apparatus.

In operation, the interior 40 of the sleeve 38 is inflated by squeezing a depressible bulb 21, FIG. 1, which is interconnected to the sleeve 30 through a tethered interconnection to a port 18, FIG. 1. Squeezing the depressible bulb 21, FIG. 1, inflates the interior 40 of the sleeve 38 as air/fluid is pushed through the interconnecting hose 19, FIG. 1, into the sleeve interior 40. As the sleeve 38 is inflated, pressure changes are sensed by the movement mechanism within the gage housing 30 as follows.

Air entering the sleeve interior 40 is also caused to enter the gage 30 through the socket opening 42 and also through an opening 68 provided at the bottom of the gage. Entering air causes axial upward movement of the movable surface 116 of the diaphragm 114 which is imparted to the end of an axially displaceable shaft member 130 which is vertically supported therein. The shaft member 130 is also caused to rotate as well as translate due to constraints provided by a helically wound ribbon spring 134 made from beryllium copper or other similar spring material. The ribbon spring 134 is supported at one upper end to an intermediate portion of the shaft member 130 and at an opposite end to a fixed portion of the gage 30.

Rotation of the shaft member 130 due to the flexion of the helically wound ribbon spring 134 causes corresponding circumferential movement of an attached indicating member 136 attached to an extending end of the shaft member. The indicating member 136 is disposed in relation to the indicia of the dial face 82. Additional details regarding the herein described movement mechanism described herein are provided in U.S. Pat. Nos. 5,966,829 and 6,120,458, the entire contents of each being herein incorporated by reference, while further details relating to the socket and the direct interconnection of a gage to an inflatable sleeve are provided in previously incorporated U.S. Ser. No. 09/669,474.

Figure 3:
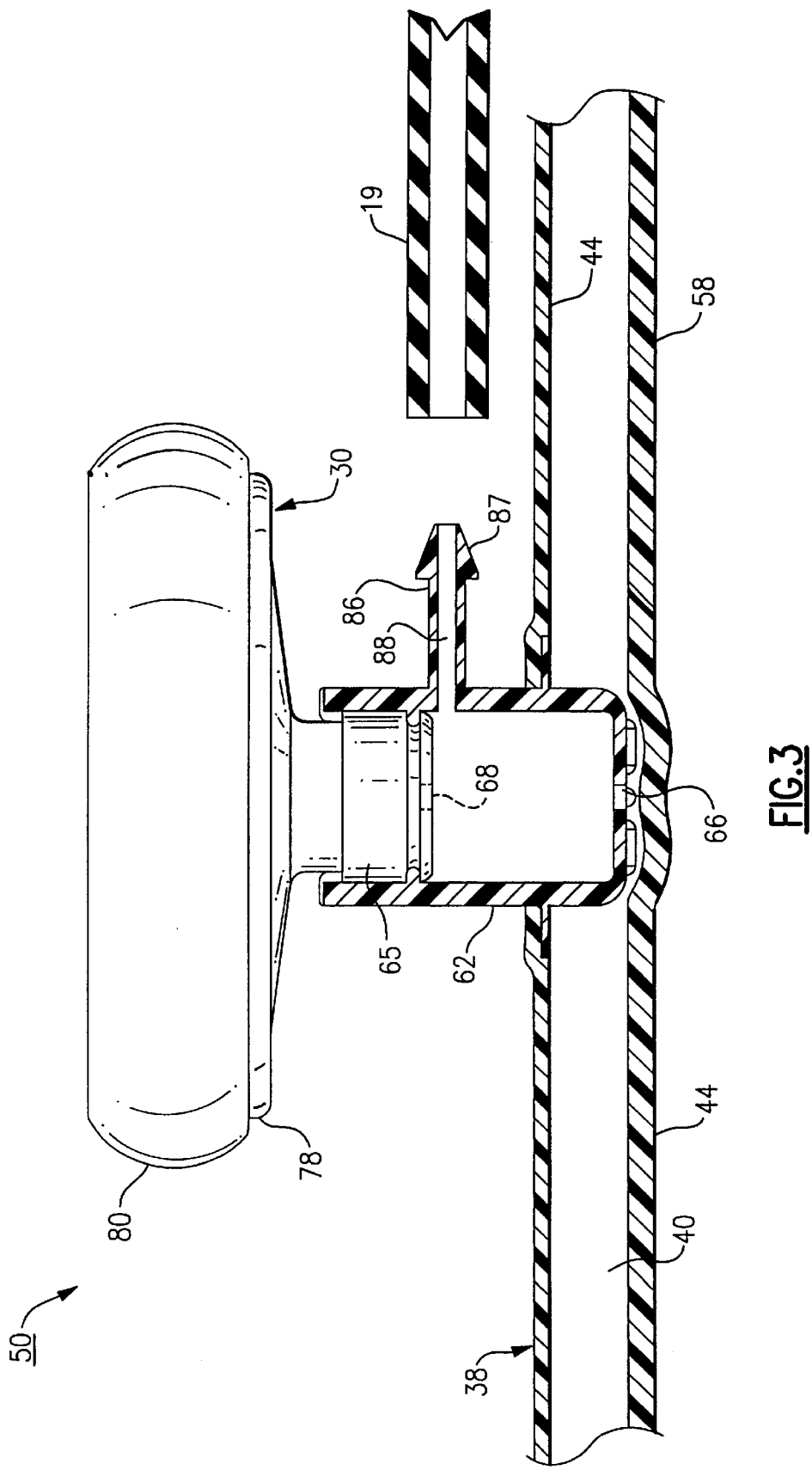
FIG. 3 is a partial side elevational view of a blood pressure measuring apparatus according to a first embodiment of the invention.

Having supplied the preceding background and now referring to FIG. 3, there is shown a blood pressure measuring apparatus 50 made in accordance with a first embodiment of the invention. For purposes of the following discussion, similar parts are identified with the same reference numerals for the sake of convenience.

An inflatable sleeve 38 includes an interior 40, the sleeve being made from a pair of sleeve portions 44, which are interconnected together as previously described. A specific type of sleeve which can be used for these purposes is described in previously incorporated U.S. Pat. No. 6,036,718. As previously noted, however, it should be apparent that other bladderless and bladder-type sleeve designs can be utilized.

One of the sleeve portions 44 includes a socket 62 which is attached by welding or other means to a slot, the socket being fluidly interconnected to the interior 40 of the sleeve 38 through an opening 66. The socket 62 extends above the plane of the exterior of a sleeve portion 44 and includes a laterally projecting receiving port 86 which is sized to receive a depending end of a hose 19 of a pneumatic assembly 20, FIG. 1. The laterally projecting receiving port 86 includes a through passage 88 which extends to the socket interior and includes a barb 87 onto which the hose can be attached.

The pneumatic assembly 20 includes a flexible depressible bulb 21, FIG. 1, which is attached through the hose 19 and further includes bleed valve 27, FIG. 1. Air which enters the socket 62 from the pneumatic assembly is communicated to the interior 40 of the sleeve 38 as well as the interior of the attached gage 30.

The gage housing 30 according to this embodiment includes a movement mechanism (not shown in this Fig.) as described above such that air entering the socket 65 is directed into the sleeve interior 40 through opening 66 and into the interior of the gage 30 through opening 68.

Figure 4:
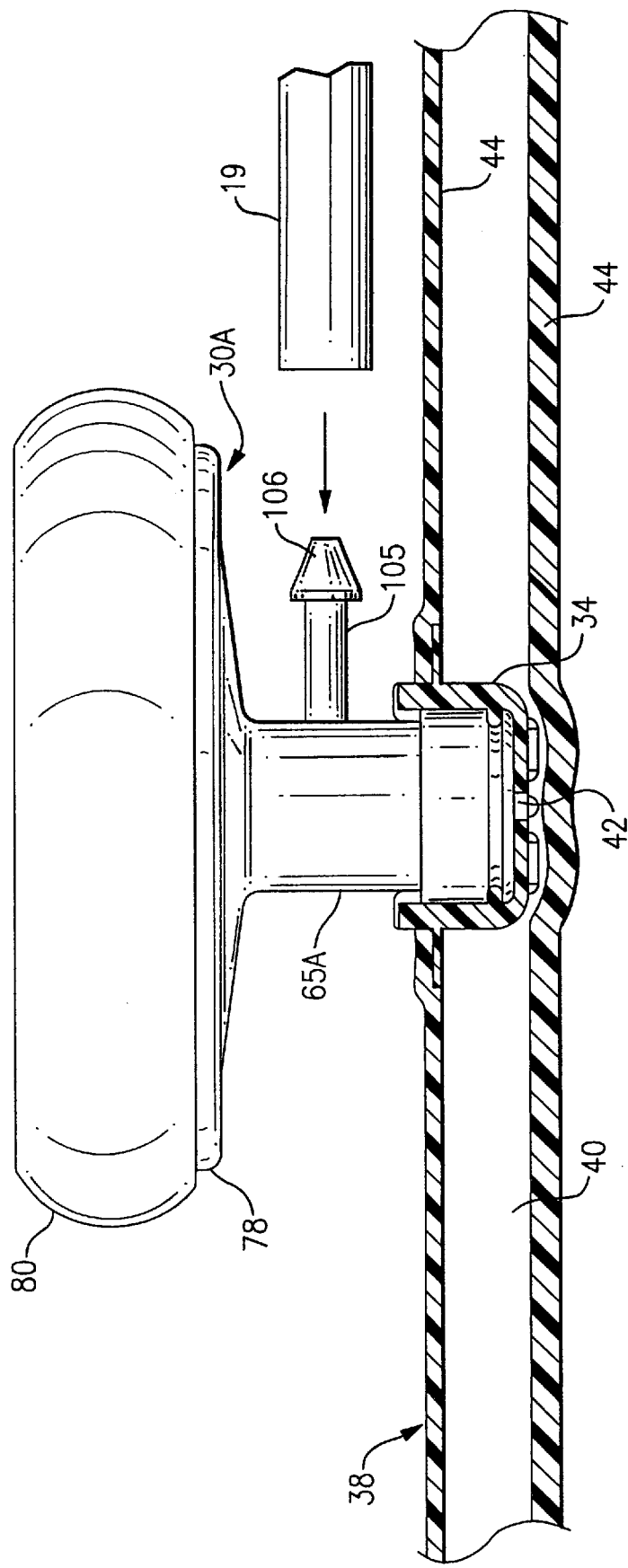
FIG. 4 is a partial side elevational view of a blood pressure measuring apparatus according to a second embodiment of the invention.

According to a second embodiment as shown in FIG. 4, a laterally projecting receiving port 106 can be similarly provided on the mating end 65A of a similar gage 30A, the receiving port being disposed a predetermined distance from the lower end of the gage to permit seating of the gage 30A within the socket 34 of the inflatable sleeve 38.

In operation, the apparatus functions similarly wherein the hose 19 of the pneumatic assembly 20, FIG. 1, is attached to the barb 106 of the receiving port 105. Squeezing the bulb 21, FIG. 1, permits air to be directed into both the lower portion 65A of the gage 30A and the interior 40 of the sleeve 30 based on the attachment of the gage to the socket 34.

Following inflation in either embodiment, the bleed valve 27, FIG. 1, permits deflation of the inflatable sleeve 38 and a blood pressure measurement can be made using a stethoscope (not shown) which can be placed over the brachial artery ( in the case in which the limb is an arm, not shown) done in a conventional manner.

Other embodiments utilizing the inventive concepts described herein are possible. For example and referring to FIG. 5, an inflatable sleeve 200 similar to that previously described can be provided with a pair of sockets 202, 204, each of the sockets being sized to directly accept the mating or engagement end 65, FIG. 3, of a gage housing 30, FIG. 3, as previously described. Each of the sockets 202, 204 can, as in this instance, be similarly constructed with the gage 30, FIG. 3 including a laterally extending receiving port 86 such as previously described. Alternately, either or both of the sockets 202, 204 could include a laterally projecting receiving port 105, such as previously shown in FIG. 4.

Providing a pair of sockets 202, 206 on the inflatable sleeve 200 provides significant versatility in the location of a gage 30, 30A which is directly mounted thereupon.

According to yet another alternate variation, a port adapter 210 is illustrated in FIG. 6 which can also be used in conjunction with the sleeve 200, the adapter 210 being fitted into one of the sockets 202, 204 to accept, for example, a hose 19 such as shown in FIG. 1 therein and a gage 25 in the other of the sockets. The port adapter 210 includes a barb 212 which matingly receives the hose 19, FIG. 1, and a channel 216 defining a fluid path to the interior of the sleeve 200. The adapter 210 includes a plug-like end 220 which permits fluid-seal attachment to one of the sockets 202, 204.

PARTS LIST FOR FIGS. 1–6

10 blood pressure measuring apparatus
14 inflatable sleeve
18 port
19 hose
20 pneumatic assembly
21 depressible bulb
22 port
23 hose
24 hook and loop fasteners
25 gage
27 bleed valve
28 indicating member
29 dial face
30 gage
30A gage
32 blood pressure measuring apparatus
34 socket
38 sleeve
40 interior
42 bottom opening
44 sleeve portions
50 blood pressure measuring apparatus
62 socket
65 engagement portion
65A engagement portion
66 opening
68 opening
78 upper portion
80 peripheral bumper
82 dial face
86 laterally projecting receiving port
87 barb
88 through passage
105 receiving port
106 barb
114 diaphragm
116 movable surface
130 axially displaceable shaft member
134 ribbon spring
200 sleeve
202 socket
204 socket
210 port adapter
212 barb
216 channel
220 plug-like end While the present invention has been described with reference to the preferred embodiments, it should be readily apparent that modifications and variations are possible without departing from the intended scope of the invention as defined by the claims.

We claim:

1. A blood pressure measuring apparatus comprising:

an inflatable sleeve adapted to be wrapped about a limb of a patient, said sleeve including an interior and at least one socket provided in an exterior surface of said sleeve, said socket including an opening that is fluidly and directly connected to the interior of said inflatable sleeve;

a gage housing having an integral mating end releasably fitted directly into said at least one socket provided on the exterior surface of said sleeve;

a pneumatic means for inflating said sleeve; and means for attaching said pneumatic means to said sleeve, said attaching means including a receiving means provided on one of said at least one socket and said mating end of said gage housing.

2. An apparatus as recited in claim 1, wherein said receiving means is provided on said socket.

3. An apparatus as recited in claim 2, wherein an axial portion of said socket extends above the exterior surface of said sleeve.

4. An apparatus as recited in claim 1, wherein said receiving means includes a port provided on the mating end of said gage housing.

5. An apparatus as recited in claim 4, wherein said port is provided a predetermined distance from an end of said mating end of said gage housing along a length thereof.

6. An apparatus as recited in claim 1, wherein said sleeve includes at least two sockets.

7. An apparatus as recited in claim 1, wherein said receiving means includes a port sized for receiving a hose from said pneumatic means.

8. An apparatus as recited in claim 1, wherein said gage housing includes an opening at a distal end of said mating end, said opening extending to the interior of said socket.

9. An apparatus as recited in claim 8, wherein said gage housing contains an indicating mechanism that is responsive to pressure changes from said sleeve interior.

* * * * *